(12) United States Patent
Noble et al.

(10) Patent No.: US 12,589,002 B2
(45) Date of Patent: Mar. 31, 2026

(54) SYSTEMS AND METHODS FOR PREPARING A MENISCAL TISSUE FOR IMPLANT

(71) Applicant: ARTHREX, INC., Naples, FL (US)

(72) Inventors: Shane Noble, Naples, FL (US); Robert Benedict, Naples, FL (US); G. Joshua Karnes, Naples, FL (US); Anthony Orozco, Naples, FL (US); Brian Cole, Naples, FL (US)

(73) Assignee: Arthrex, Inc., Naples, FL (US)

( * ) Notice: Subject to any disclaimer, the term of this patent is extended or adjusted under 35 U.S.C. 154(b) by 631 days.

(21) Appl. No.: 17/998,205

(22) PCT Filed: May 10, 2021

(86) PCT No.: PCT/US2021/031567
§ 371 (c)(1),
(2) Date: Nov. 8, 2022

(87) PCT Pub. No.: WO2021/231292
PCT Pub. Date: Nov. 18, 2021

(65) Prior Publication Data
US 2023/0218403 A1    Jul. 13, 2023

Related U.S. Application Data

(60) Provisional application No. 63/024,411, filed on May 13, 2020.

(51) Int. Cl.
*A61F 2/38*        (2006.01)
*A61F 2/28*        (2006.01)
(Continued)

(52) U.S. Cl.
CPC .......... *A61F 2/3872* (2013.01); *A61F 2/3094* (2013.01); *A61F 2/4644* (2013.01);
(Continued)

(58) Field of Classification Search
CPC .... A61F 2/3872; A61F 2/3094; A61F 2/4644; A61F 2002/2839; A61F 2002/30158;
(Continued)

(56) References Cited

U.S. PATENT DOCUMENTS 9,918,769 B2 *    3/2018    Provencher ........... A61F 2/4644
10,736,755 B2 *    8/2020    Bosworth .......... A61B 17/1764
(Continued)

OTHER PUBLICATIONS

Extended European Search Report for European Patent Application No. 21803203.5, mailed Apr. 30, 2024.
(Continued)

*Primary Examiner* — Jonathan G Riley
(74) *Attorney, Agent, or Firm* — Lisa Hillman; Lathrop GPM LLP

(57)        ABSTRACT

Systems and methods here include a meniscal allograft with a bone block and a technique for making a desired shape in the bone block to be used to implant in a patient. A clamp and/or jig arrangement are disclosed that are able to secure the tissue and allow three corresponding cuts to the tissue using the clamp as a guide to a saw to obtain the desired shape.

14 Claims, 17 Drawing Sheets

(51) Int. Cl.
　　　*A61F 2/30* 　　　(2006.01)
　　　*A61F 2/46* 　　　(2006.01)
(52) U.S. Cl.
　　　CPC ................ *A61F 2002/2839* (2013.01); *A61F 2002/30158* (2013.01)
(58) Field of Classification Search
　　　CPC ...... A61F 2002/2835; A61F 2002/3028; A61F 2/28; A61F 2230/0026; A61F 2230/0063; A61B 17/15; A61B 17/1764
　　　See application file for complete search history.

(56) 　　　　　References Cited

U.S. PATENT DOCUMENTS

| | | | |
|---|---|---|---|
| 2001/0002446 A1 | 5/2001 | Plouhar et al. | |
| 2002/0151975 A1* | 10/2002 | Farr, II .............. | A61B 17/1675 |
| | | | 623/14.12 |
| 2004/0034419 A1* | 2/2004 | Carter ................... | A61B 17/15 |
| | | | 623/23.63 |
| 2009/0234452 A1 | 9/2009 | Steiner et al. | |
| 2013/0096680 A1* | 4/2013 | Ribeiro ................ | A61F 2/4644 |
| | | | 606/88 |
| 2016/0270933 A1* | 9/2016 | Bosworth ................ | A61F 2/28 |
| 2016/0374695 A1 | 12/2016 | Dacosta et al. | |
| 2018/0325699 A1 | 11/2018 | Bosworth et al. | |
| 2020/0405326 A1* | 12/2020 | Bosworth ............. | A61B 90/06 |
| 2023/0218403 A1* | 7/2023 | Noble ................... | A61F 2/3094 |
| | | | 83/56 |

OTHER PUBLICATIONS

International Search Report of the International Search Authority issued in International Appl. No. PCT/US2021/031567, 4 pages, dated Oct. 20, 2021.

Written Opinion of the International Search Authority issued in International Appl. No. PCT/US2021/031567, 4 pages, dated Oct. 20, 2021.

* cited by examiner

301

1320

1302

1310

1330

1312

1322

1304

1300

SYSTEMS AND METHODS FOR PREPARING A MENISCAL TISSUE FOR IMPLANT

PRIORITY

This application is a 371 of International Application No. PCT/US2021/031567, which was filed May 10, 2021, which claims the benefit of U.S. Ser. No. 63/024,411, which was filed on May 13, 2020, and which are incorporated by reference herein in their entireties.

BACKGROUND

One way to perform an anatomical reconstruction of the meniscus is to shape a bone block of a meniscal allograft into a keyhole shape to match a corresponding keyhole groove prepared through the cortical and cartilagenous surface of the tibial plateau. A bone plug or block for the meniscal allograft is then fed into the keyhole groove, such that the meniscal allograft is mounted on the tibial plateau and secured without transosseous sutures.

Although the above-described technique is an improvement over prior meniscal allograft technique, the keyhole shape of the allograft implant is difficult to reproduce and necessitates a long preparation time, multiple clamping that can damage tissue, and difficult preparation. Thus, although the keyhole technique described above is an improvement over prior meniscal allograft techniques, it would be desirable to provide a meniscal transplant system and method that is more consistent, quicker to replicate, and results in less damage to the tissue.

SUMMARY

Systems and methods for preparing a meniscal tissue for implant include a jig with a base, two lower arms, and two upper arms, a clamp with a first block and a second block, the first block and second block connected by a threaded screw rod that allows the first block and second block to be moved closer or farther from one another through corresponding screw threads, three pairs of posts, a first pair of posts located on a top of the two upper jig arms, a second pair of posts located on a middle of the two upper jig arms, and a third pair of posts located on a top of the two lower jig arms, wherein the clamp first and second block are configured to mount on each of the three pairs of posts by a slot in each of the respective first and second blocks, and securing features located on an inside of each of the first clamp block and second clamp block, configured to secure a bone block and meniscal tissue. In some examples, the clamp includes a slide rod mounted in parallel to the threaded screw rod in the first and second clamp blocks. In some examples, the clamp is configured to guide sawing a meniscal tissue bone block secured in the clamp along without removing or adjusting the clamp to obtain a shape that is generally of the same shape as the clamp first block and second block, and some examples utilize securing features located on an inside of each of the first clamp block and second clamp block, configured to secure a bone block and meniscal tissue.

In some examples, the clamp first and second block have a generally trapezoidal end-on shape, the trapezoidal shape including a first side, a second bottom side, a third side, and a top side, wherein the top side includes the threaded screw rod. In some examples, the top of the two upper jig arms and the first clamp side allow for the clamp to mount to the first pair of posts on the top of the two upper jig arms. In some examples, the top of the two upper jig arms and the third clamp side allow for the clamp to mount to the second pair of posts on the middle of the two upper jig arms. In some examples, the top of the two bottom jig arms and the first clamp side allow for the clamp to mount to the third pair of posts on the top of the two lower jig arms. In some examples, the securing features on the inside of each of the first clamp block and second clamp block are spikes, and a number of securing spikes located on an inside of each of the first clamp block and second clamp block, are four on each block.

Systems and methods for preparing a meniscal tissue for implant include, mounting a bone block with meniscal tissue in a clamp once, wherein the clamp includes a first side and a second side, with a base connecting the first side and second side, wherein the first side and second side each include three outside guide edges, sawing the clamped bone block in each of three positions along the three outside guide edges without removing or adjusting the clamp, to obtain a shape that is generally a shape of the clamp first side and second side three outside guide edges. In some examples, the systems and methods further include tightening a threaded screw rod that allows the first side and the second side to be moved closer or farther from one another through corresponding screw threads, and before each of the three sawing steps, respectively mounting the clamp with the secured bone block and meniscal tissue in each of three places to a jig with a base, two lower arms, and two upper arms, the first mounting on a first pair of posts located on a top of the two upper jig arms, the second mounting on a second pair of posts located on a middle of the two upper jig arms, and a third mounting on a third pair of posts located on a top of the two lower jig arms, in some examples, the clamp first and second sides are mounted on each of the three pairs of posts by a slot in each of the respective first and second sides. In some examples, the clamp first and second sides have a generally trapezoidal, rectangular, dovetail, or circular shape when viewed end-on. In some examples, the clamp blocks include securing friction components located on an inside of each of the first clamp side and second clamp side, configured to secure a bone block and meniscal tissue when the threaded screw rod is tightened, wherein the friction components are one of a raised bumpers, scuffs, nubs, points, knurls, spikes, or set screw. In some examples, the generally trapezoidal shape includes one angle of about 65 to about 80 degrees. In some examples, generally trapezoidal and rectangular shapes include at least one angle of about 90 degrees. In some examples, the first side and the second side each include an outer frame and an inner tongue both mounted on the base, wherein each tongue is configured to flex under pressure, and wherein the first side includes a friction component and wherein the second side includes a set screw, in some examples, mounting the bone block includes tightening the set screw. In some examples, the friction component includes at least one of raised bumpers, scuffs, nubs, points, knurls, spikes, and a set screw. In some examples, the systems or methods also include placing the bone block in a slot cut jig for transportation, wherein the slot cut jig is made of metal and includes a main slot to secure the shaped bone block and an upper and lower saw slot configured to allow a user to saw a triangle shape off the shaped bone block leaving a generally rectangular shaped bone block.

BRIEF DESCRIPTION OF THE DRAWINGS

For a better understanding of the embodiments described in this application, reference should be made to the Detailed Description below, in conjunction with the following drawings in which like reference numerals refer to corresponding parts throughout the FIGS.

DETAILED DESCRIPTION

The present disclosure includes systems and methods for preparing a meniscal implant using a clamp and jig system to prepare a dovetail in the bone of the meniscus specimen. A dovetail meniscus implant can be machined from allograft cortical bone using systems and methods described herein, can produce a single piece of harvested material with the meniscus on a bone block. Alternatively, an implant can be formed of a synthetic material, such as a synthetic bone material and prepared the same way. In any case, the systems and methods described herein can allow for more accurate shaping of the meniscus tissue, to be prepared in a more repeatable manner, with only one clamp applied to the tissue, thereby reducing the amount of abrasive clamp damage to the tissue.

Figure 1:
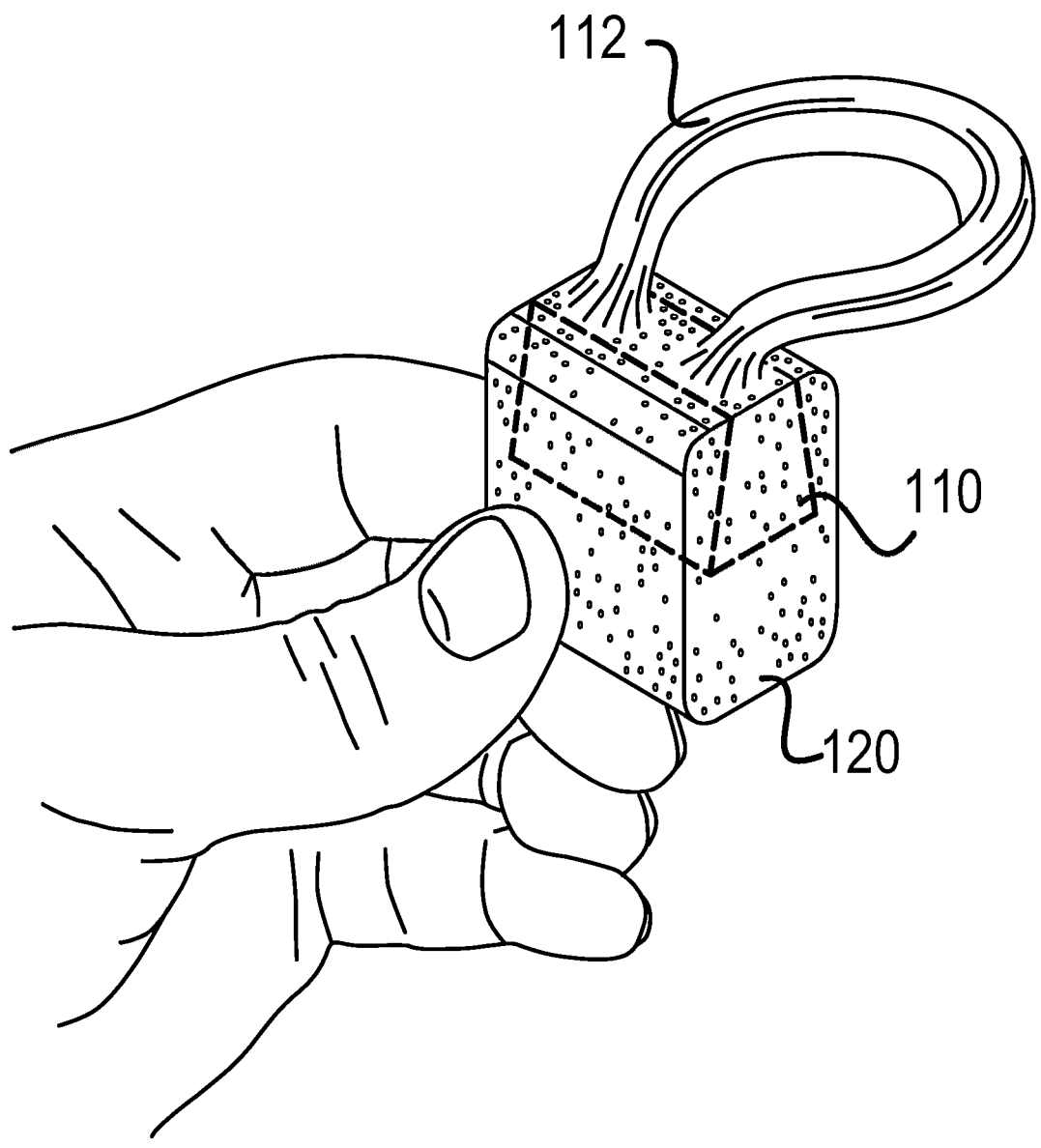
FIG. 1 is an example tissue specimen according to embodiments disclosed herein.
Figure 2:
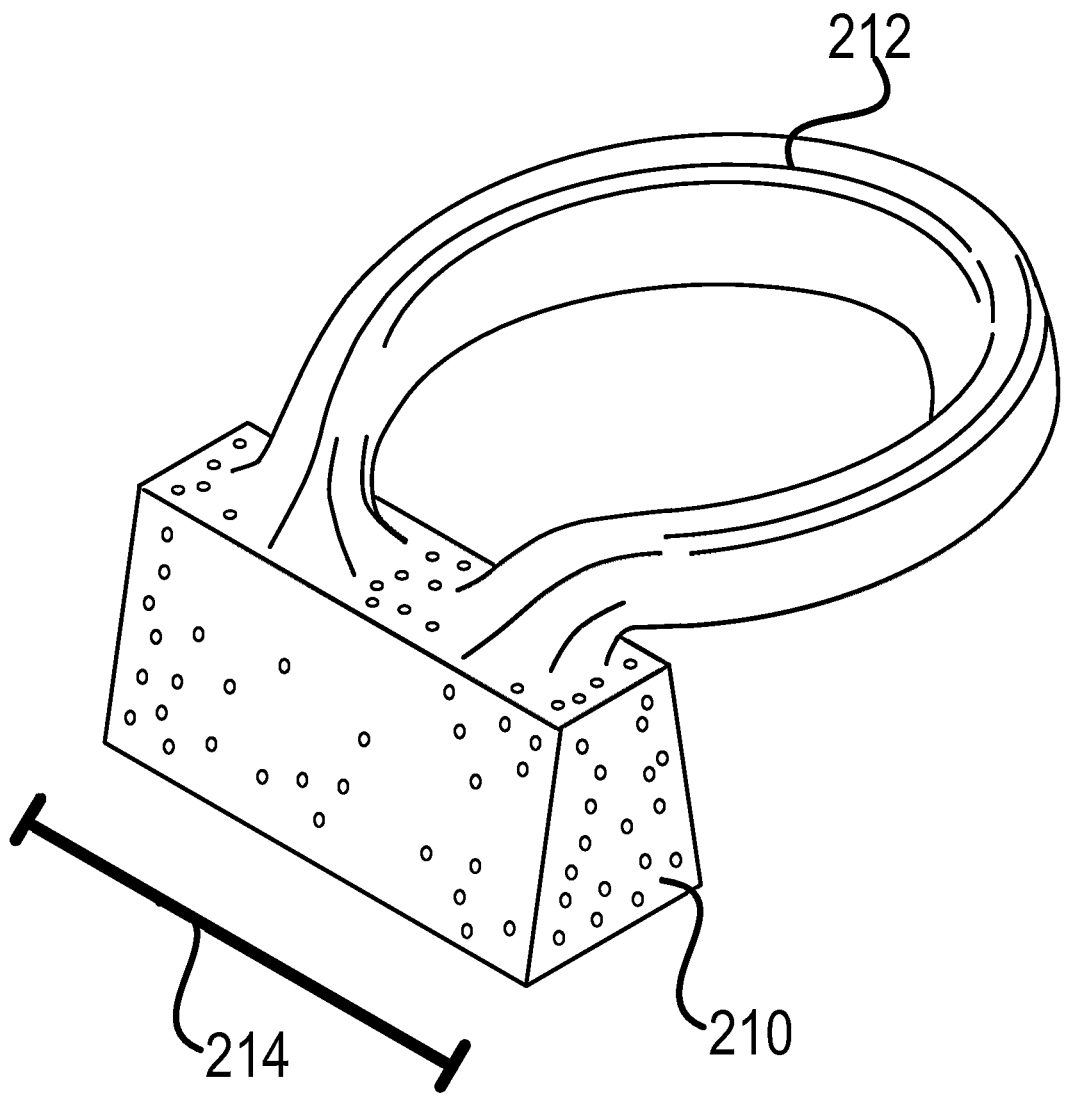
FIG. 2 is an example tissue specimen according to embodiments disclosed herein.

FIG. 1 shows an example of the bone 120 and meniscus 112 specimen from the donor. To prepare the specimen, the bone is to be shaped as shown 110 with a dovetail, or trapezoidal shape using the systems and methods here. FIG. 2 shows an example of the end result, with the dovetail shaped bone 210 and attached meniscus 212 which can be implanted in the patient as described herein. In some examples, the width of a typical bone block for implantation is about 2.16 inches (55 mm wide) 214. In some examples, the width of a typical bone block for implantation is about 1.97 inches to about 2.36 inches (about 50 mm to about 60 mm wide 214.

Example Clamp Arrangements

As described, the goal of the meniscal procedure is to prepare both a cadaver donor bone bock (or manufactured artificial replacement) attached to a meniscal tissue and corresponding feature in the receiving patient knee bone to secure the bone block and replacement meniscal tissue as shown in FIGS. 1 and 2. In order to prepare the bone attached to the meniscal tissue to fit into the bone keyhole feature in the knee, certain preparation and cuts can be made to the bone block to ensure it fits into the patient knee keyhole feature to match their shapes.

Figure 3A:
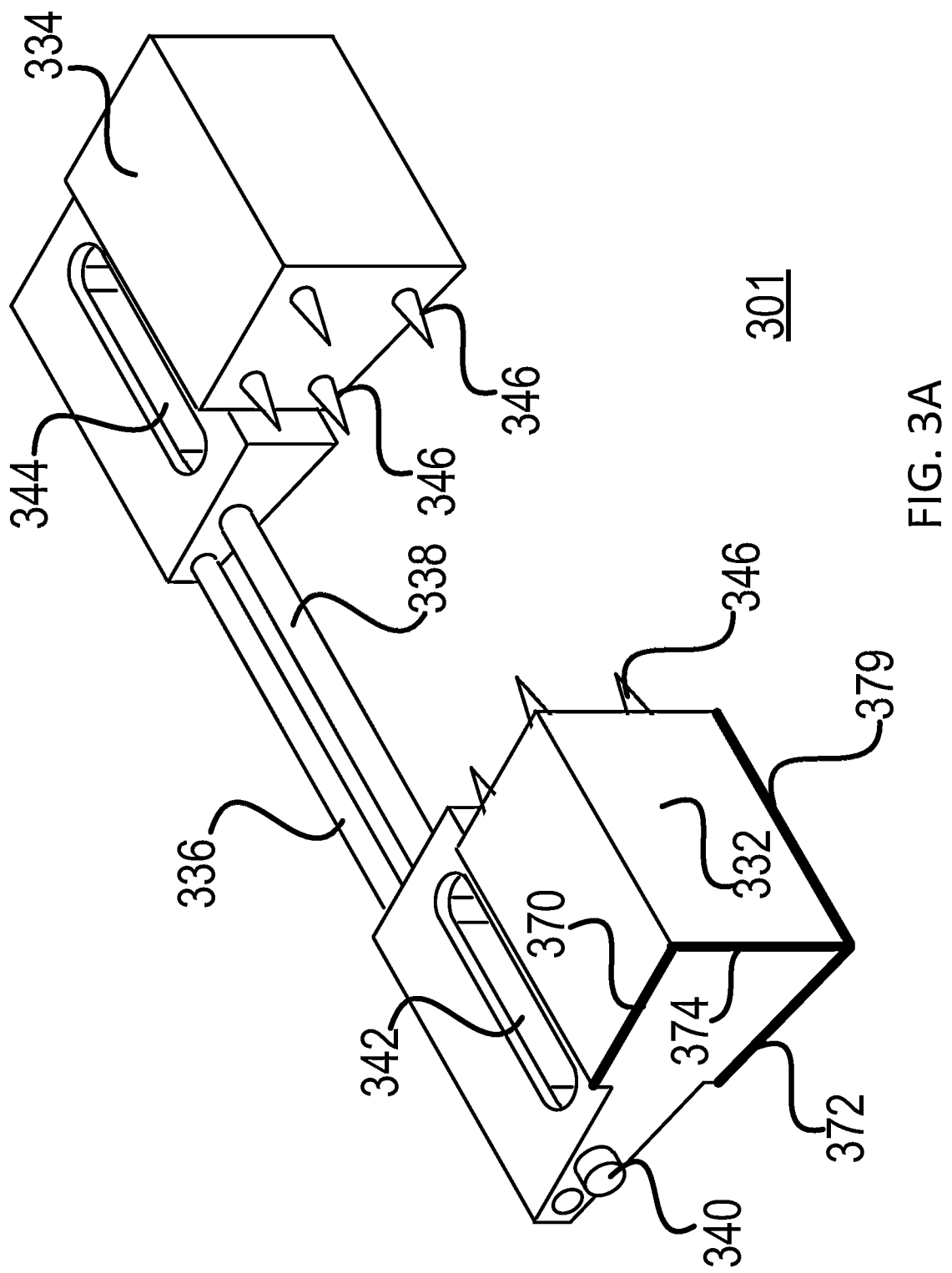
FIGS. 3A and 3B are example clamps according to embodiments disclosed herein.
Figure 3B:
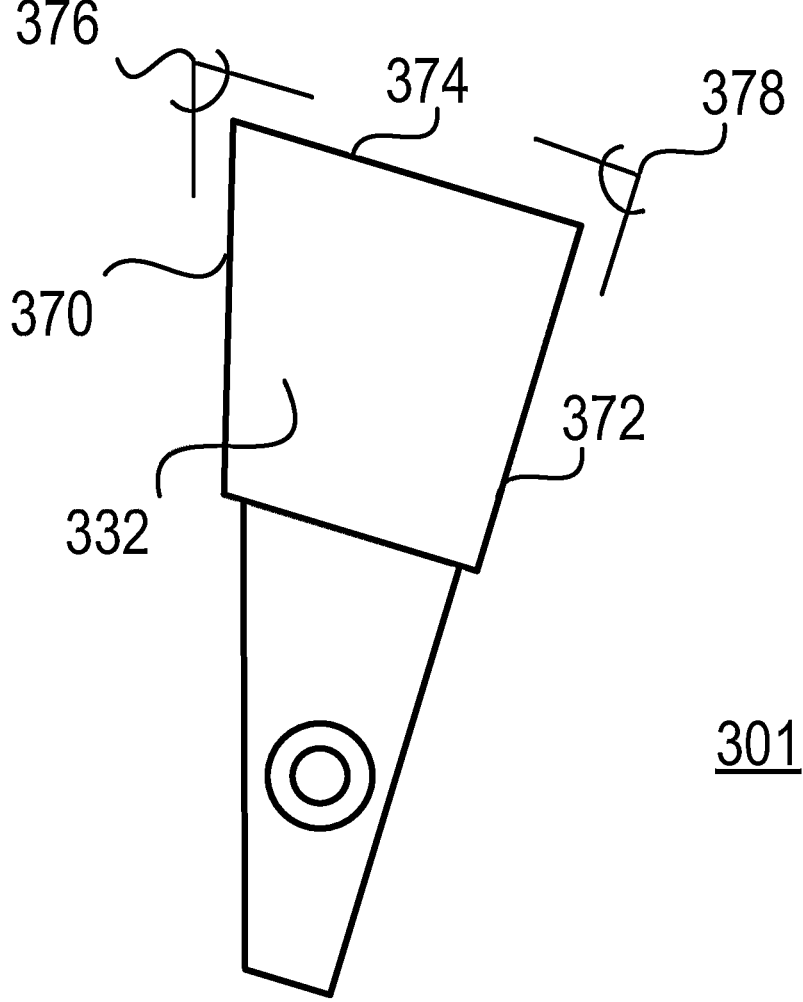

As described, in order to control the meniscal tissue and bone block during preparation, it can be useful for the human user or operator to attach a clamp arrangement to the tissue before attempting to make any cuts to the tissue. FIGS. 3A and 3B show an example clamp arrangement or mechanism 301 that can allow the human operator to more surely control the tissue, and in the systems and methods here, can allow for the clamp to fit onto specifically designed jig features, to ensure that the cuts made to the bone are accurate. By securing the clamp only once, and being able to guide all the necessary cuts to form the desired shape, the systems and methods herein allow for a more accurate tissue preparation, which is easier for the human user, and with less damage to the tissue sample used for the transplant. This is due, at least in part, to the ability for the preparation to be made with only one clamp applied one time to the tissue.

FIG. 3A shows the clamp 301 having two main blocks 332, 334 connected by a bar 336 and a screw bar 338. As discussed in FIG. 2, because a typical bone block for implantation is about 2.16535 inches (about 55 mm wide), the clamp main blocks 332, 334 can be able to surround and clamp about a 2.16535 inches (about 55 mm) tissue specimen, meaning the bar 336 and screw bar 338 must be able to accommodate this size. In some examples, the bar 336 and a screw bar 338 are about 2 inches long (about 50.8 mm). In some examples, the bar 336 and a screw bar 338 are about 1.5 to about 3 inches (about 38.1 mm to 76.2 mm) long. In the example of FIG. 3A, the two main blocks 332, 334 are trapezoidal in shape, or dovetail in shape when viewed end-on, with the three sides 370, 372, 374 forming the dovetail or general trapezoid shape. As will be discussed, it is this shape that an operator can use as a guide to cut the bone to form the correct shape in the bone specimen. In some examples, each block 332, 334, can be about 0.75 inches (about 19 mm) long 379. In some examples, each block can be about 0.5 to about 1.5 inches (about 12.7 mm to 38.1 mm) long 379.

The description herein is not limited to a trapezoidal shaped clamp to make a corresponding trapezoidal shaped tissue block. In some examples, a trapezoidal shape is not used, and a generally rectangular shape is used as the end-on clamp shape instead. In some examples, other shapes such as a dovetail, a shape with one straight and one slanted side, or two straight edges can be used as the end-on clamp shape. In some examples, a generally circular shape can be used as the end-on clamp shape. In such examples, the bone block tissue can be prepared with a desired shape by utilizing a clamp with a corresponding shape when viewed end-on. The example showing a generally trapezoidal shape is not intended to be limiting.

FIG. 3A shows the example clamp 301 where the two main blocks 332, 334, are able to be configured closer to one another or farther away from one another, yet retain the same orientation relative to one another due to the bar 336 that can be fixedly attached to one of the blocks 332, 334 and not fixedly attached to the other, so as to be able to slide through a hole of the not fixedly attached block 332, 334. Additionally or alternatively, a screw bar 338 can also or independently separate the two main blocks 332, 334. In such a way, a screw bar 338 can include threads that can mate with corresponding threads in one or both of the main blocks 332, 334, to allow for the operator to tighten or loosen the screw bar 338 by a knob 340 or end of the screw bar 338. In such a way, the two main blocks 332, 334, can be positioned farther away from one another on the bar 336, or can clamp by being positioned closer together on the bar 336 and can tighten a specimen which can be clamped between the two main blocks 332, 334 as described herein.

FIG. 3A also shows an example clamp 301 with pointy spikes 346 attached to the inside of the blocks 332, 334. Such a spike 346 can be any kind of raised portion which can help secure the specimen (shown in FIG. 7) between the main blocks 332, 334, and help them not slide, slip, rotate, or otherwise move when the main blocks 332, 334, are clamped to the tissue specimen, and tightened by the screw bar 338. Any kind of raised bumpers, scuffs, nubs, points, knurls, spikes, or other friction features alone or in combination, can be used to help secure the tissue between the main blocks 332, 334, and the depiction of spikes 346 is not intended to be limiting. And any number of such features on each inside of the blocks 332, 334 can be used, the example showing four each in FIG. 3A is not intended to be limiting, two, three, four, five, six, seven, or more features can be used in various examples, in any combination.

FIG. 3A also shows the example clamp blocks 332, 334 including slots 342, 344. Such slots can allow for corresponding pins, pegs, and/or posts on the jig (not shown) to secure the clamp 301 and tissue, in a particular orientation for preparation and sawing. The slots 342, 344 are elongated due to the ability of the clamps to be tightened or loosened, to move the blocks 332, 334 together or farther apart, depending on the screw 336 tightening or loosening. In some examples, the slots 342, 344 are about 0.5 inches (about 12.7 mm) long. In some examples the slots 342, 344 are about 0.25 to about 1 inch (about 6.35 mm and 25.4 mm) long.

In some method examples, once the clamp is positioned on the tissue, cuts to the tissue, which follow the sides of the clamp can be made without a jig. Such an example can use the clamp arrangement found in FIG. 3A. In such examples, the slots 342, 344 are not present or are not utilized in performing the preparation of the tissue specimen. In such examples, a user can hold the clamped tissue and administer the cuts needed without utilizing a jig arrangement. Saws such as a sagittal saw can be useful in such examples, and by using such a saw, the jig arrangement can be unnecessary for tissue preparation.

FIG. 3B shows an end-on view of a clamp 301. For examples using a jig combination, the main block 332, has dimensions that work with the jig (See FIGS. 4, 5, 8-11) to hold the tissue specimen at specific angles to allow a saw to cut the bone block to dimensions useful for implantation. Such a shape is the shape made of the end-on view of the clamp blocks 332. In some examples, the first side 370 of the clamp 332 can be 0.4 inches (about 10.16 mm) long. In some examples, the first side 370 can be about 0.3 to about 0.5 inches (about 7.62 mm and 12.7 mm) long.

For example, the second, middle, bottom/top side 374 of the clamp 332 can be about 0.388 inches (about 9.855 mm) long. In some examples, the middle bottom/top side of the clamp 374 can be about 0.25 to about 0.5 inches (about 6.35 mm and 12.7 mm) long.

In some examples, the third side 372 of the clamp 332 can be about 0.375 inches (about 9.525 mm) long. In some examples, the third side 372 can be about 0.3 to about 0.45 inches (about 7.62 mm and 11.43 mm) long.

In some examples, the angle 376 between the first side 370 and the second, middle side 374 of the clamp 332 can be about 73 degrees. In some examples, the angle 376 between the first side 370 and the second, middle side 374 can be about 60 to about 85 degrees.

In some examples, the angle 378 between the third side 372 and the second, middle side 374 of the clamp 332 can be about 90 degrees. In some examples, the angle 378 between the third side 372 and the second, middle side 374 can be about 80 to about 100 degrees.

The clamp and all its components described herein can be made of any material suitable for preparing the tissue as described. The material can be sturdy, solid, easy to clean and sterilize, and resilient to corrosion. In some examples, the clamp can be made of metal such as aluminum, steel, iron, brass, copper, and/or an alloy of any of these or other metals, fiberglass, carbon fiber, ceramics, or other non-metal material alone or in any combination. The jig described herein, should it be used, can be made of the same or similar material as the clamp.

Jig Examples

To prepare a meniscal bone block, a saw can be used to trim away excess tissue from the bone block as shown in FIG. 1, leaving the desired shape that corresponds to the patient knee keyhole feature as shown in FIG. 2. In some examples, in order to ensure that each cut in the tissue is made at the correct angle and the correct side of the tissue, a jig and clamp mechanism described here can be useful to the human operator to align the saw blade to the tissue for a cut. Such a shape can be the shape of the end-on view of the clamp as described, and used as a guide for a saw to cut the bone. Any number of saws can be used for this purpose including but not limited to a band saw, a scroll saw, a sagittal saw, blade saw, hand saw, and/or any other type of saws.

Figure 4A:
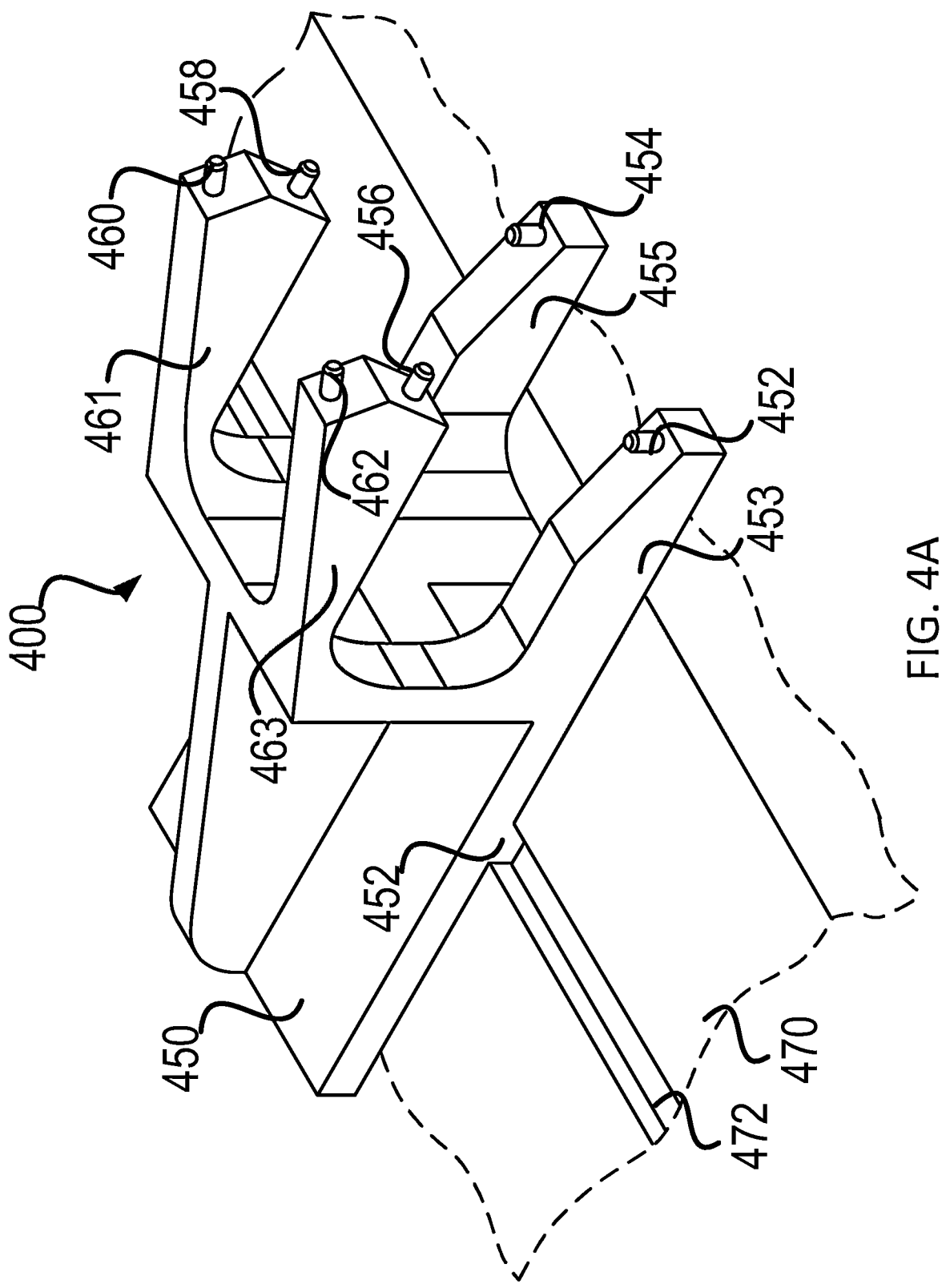
FIGS. 4A and 4B are example jigs according to embodiments disclosed herein.
Figure 4B:
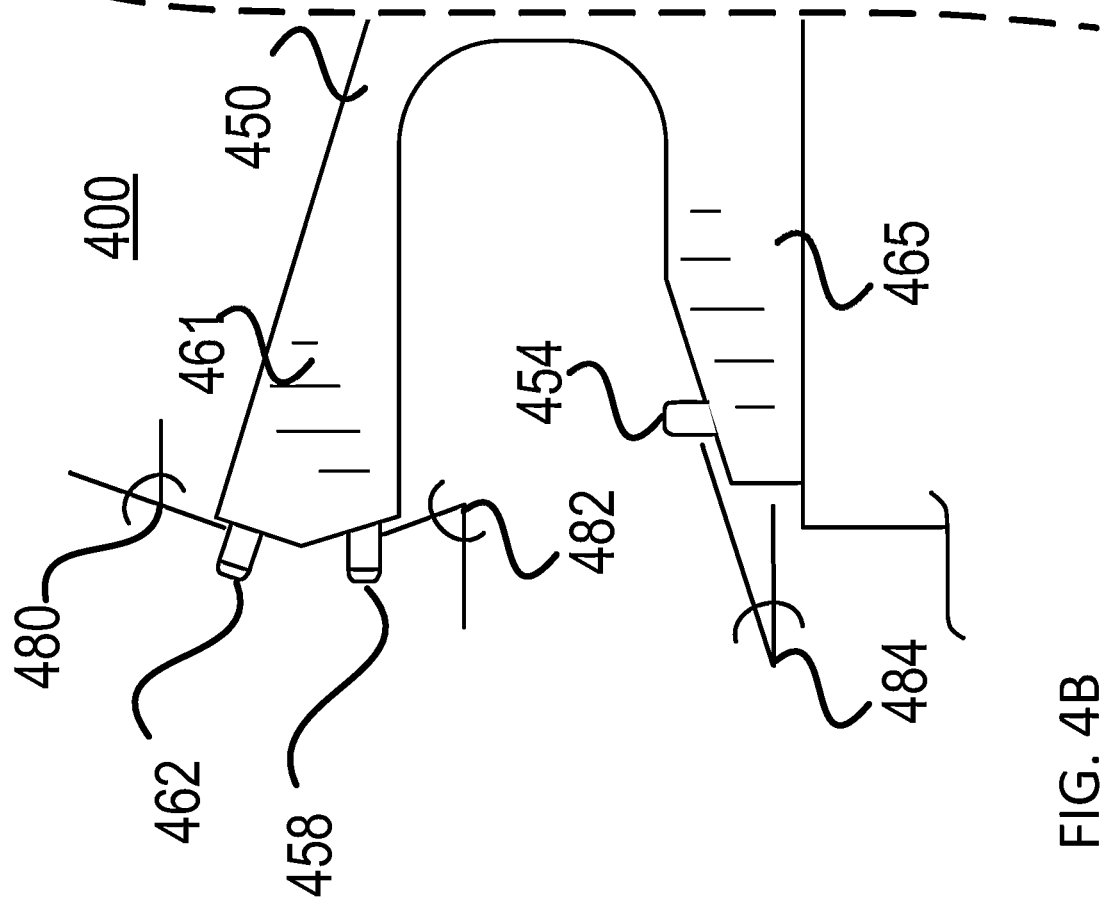

FIGS. 4A and 4B show examples of the jig arrangement that can be used in coordination with the clamp as shown in FIGS. 3A and 3B to hold the clamp and tissue at particular angles on different pin, peg, and/or post arrangements, so that the saw (as described in FIGS. 9-11) can cut the bone to form the desired shape.

Figure 9:
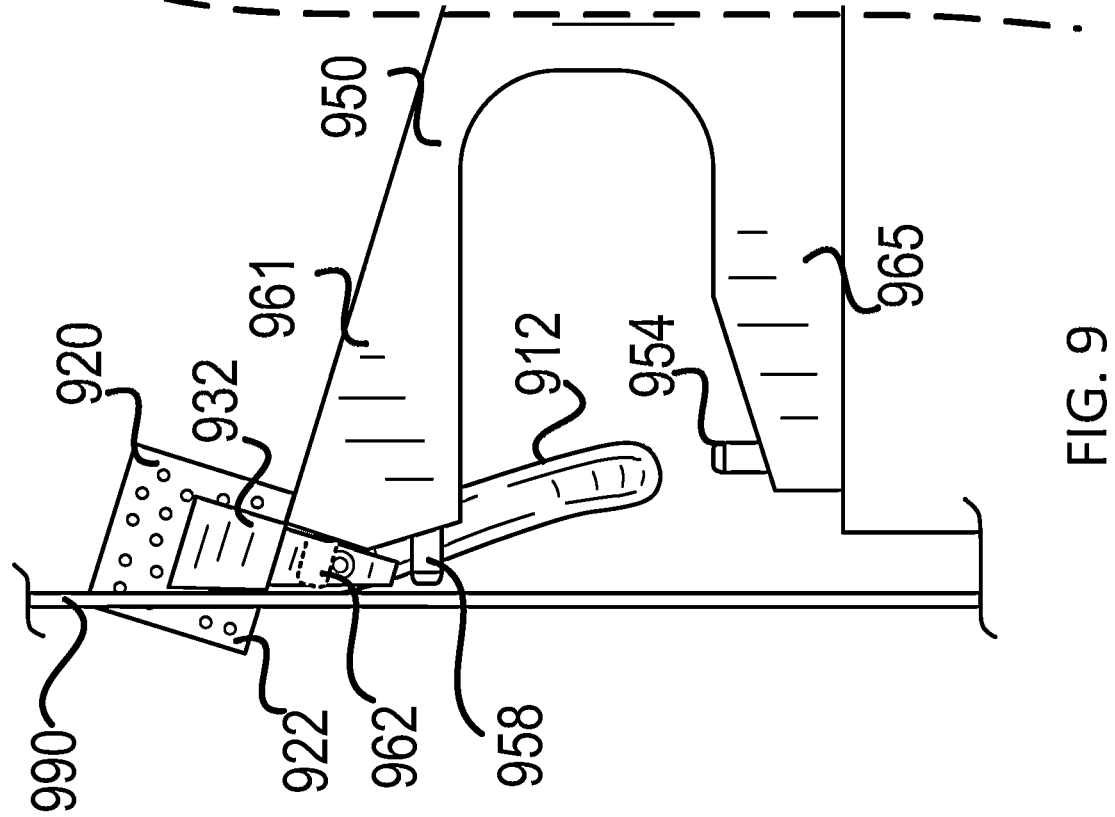
FIG. 9 is an example showing preparation of the specimen according to embodiments disclosed herein.
Figure 10:
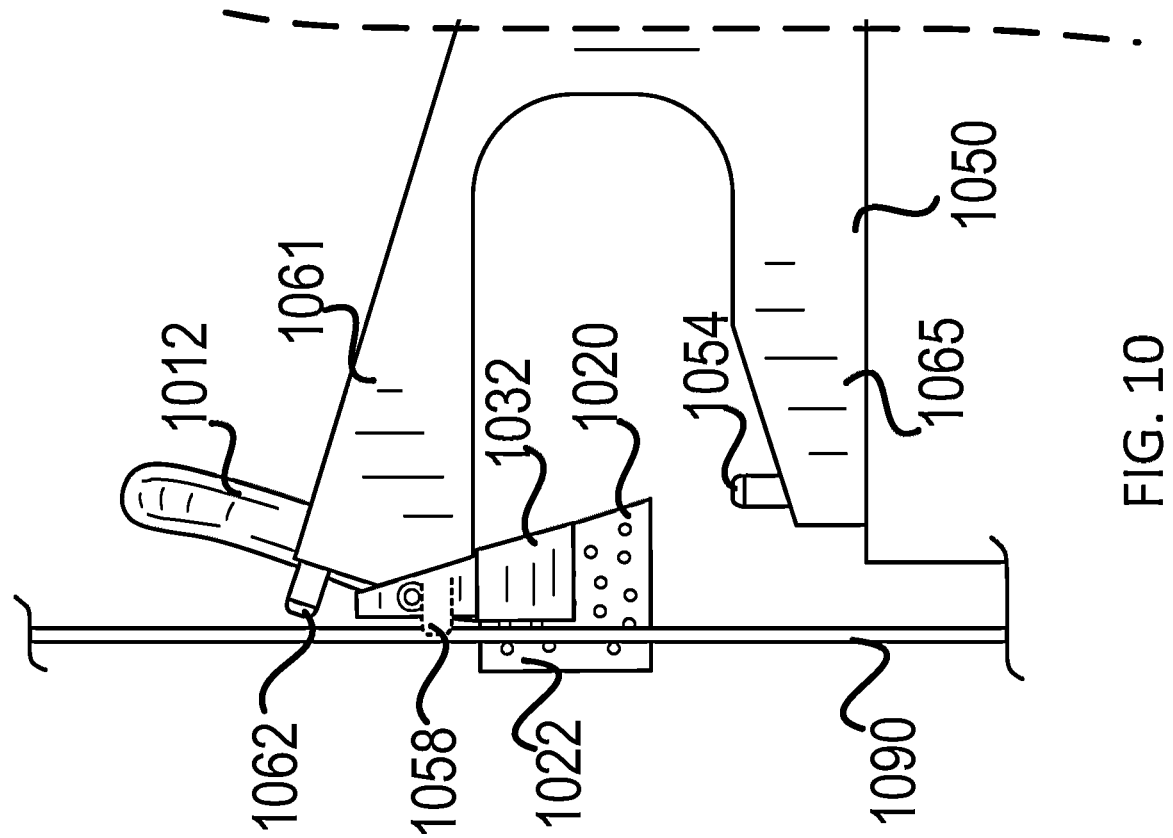
FIG. 10 is an example showing preparation of the specimen according to embodiments disclosed herein.
Figure 11:
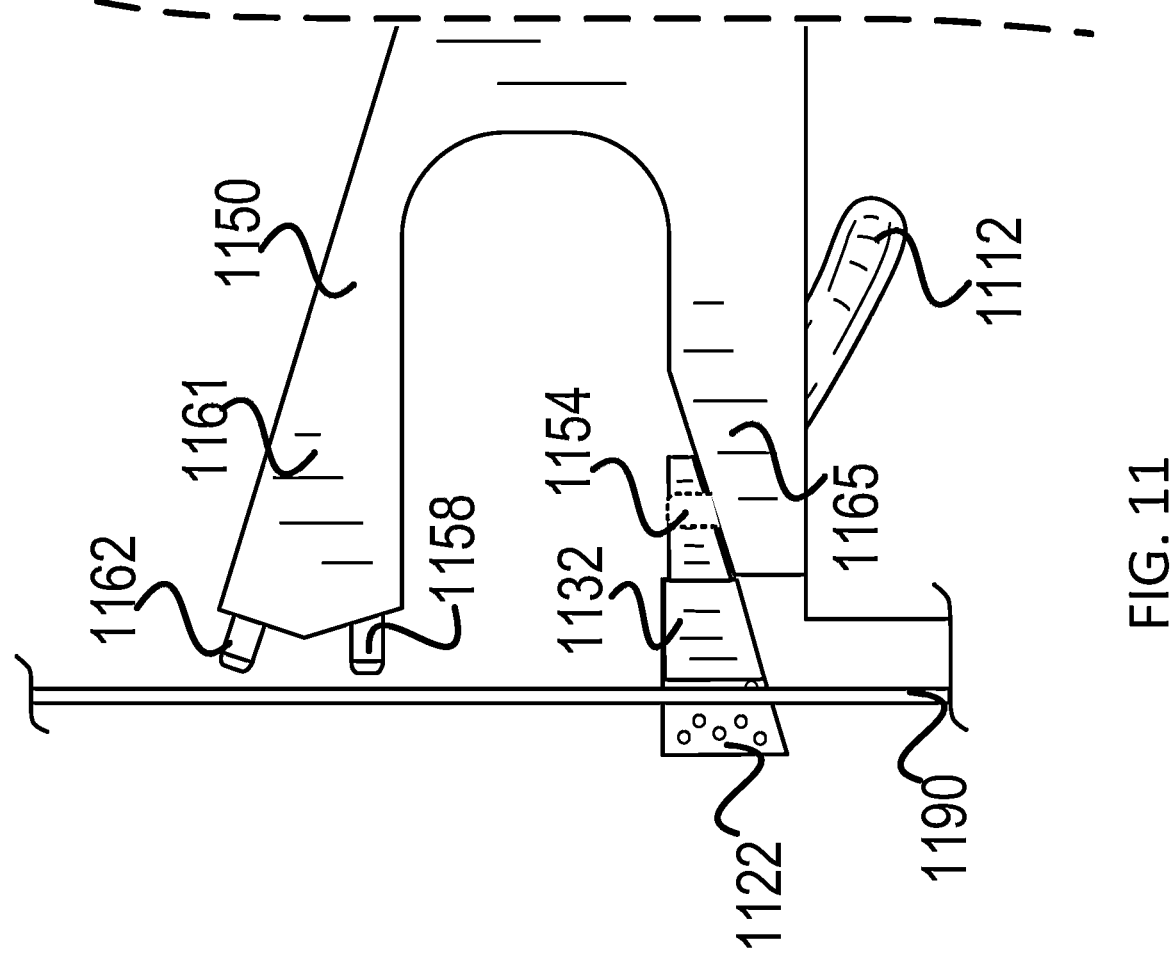
FIG. 11 is an example showing preparation of the specimen according to embodiments disclosed herein.

The jig arrangement in FIG. 4A shows the main base 450 resting on a surface 470. The example shows a groove 472 cut in the surface 470 with corresponding tongue section 452 on the base 450 to keep the jig 400 from moving, but such arrangements are optional. Any arrangement of clamps, tongue-and-groove, bolts, or other secure features can be used to hold the jig 450 in place during operation and relative orientation to a saw (as shown in FIGS. 9-11).

The jig 400 includes the main base 450 as well as four arms, two lower arms 453, 455 and two upper arms 461, 463. On each arm are formed or attached pins, pegs, and/or posts that allow for the mounting of the clamp through the clamp slots as described herein. For example, on each of the lower arms 453, 455, one post 452, 454 is mounted on each of the lower arms 453, 455 such that the posts 452, 454 are facing a generally upward direction. The upper arms 461, 463 each include two sets of posts, two posts 462, 456 on one arm 463 and two posts 458, 460 on the other arm 461. In total then, on one jig base 450, six posts, three on each side are arranged. In some examples, different numbers of posts can be used, in different orientation, to match or mate with the shape of the clamp as described herein, to effectuate a resulting orientation for the saw cuts as described.

Configuration of the posts on the jig and the slots on the clamp are merely intended as examples, and are not intended to be limiting. In some examples, the clamp can include posts, and the jig can include slots, such that similar mounting as shown in this description can be arranged, with the slots and posts on the other component parts. Other features that can be used to mount the clamp and jig can include but are not limited to hooks and eyes, magnets, tongue and groove, or other mating features, alone or in combination.

FIG. 4B shows a side-on view of the jig 400 with dimensions and examples shown to allow for the clamp (not shown) to be mounted to the three pairs of posts to cut the bone block into a desired shape as described herein. (See FIGS. 9-11) FIG. 4B shows that the upper arm 461 of the main jig base 450 has two surfaces upon which the two posts are mounted 462, 458. The first top posts 462 (of which only one is shown in the side-on view of FIG. 4B) is mounted to or part of a surface that is set at an angle 480 of 73 degrees from the horizontal. In some examples, the first top post 462 mounted to or part of a surface that is set at an angle 480 of about 65 to about 80 degrees from the horizontal.

The second set of posts 458 on the top arm 461 (of which only one is shown in the side-on view of FIG. 4B) is mounted to or part of a surface that is set at an angle 482 of 73 degrees from the horizontal, in the opposite direction from the surface upon which the first set of posts are attached. In some examples, the second top post 458 mounted to or part of a surface that is set at an angle 482 of about 65 to about 80 degrees from the horizontal.

The third set of posts 454 on the bottom arm 465 (of which only one is shown in the side-on view of FIG. 4B) is mounted to or part of a surface that is set at an angle 484 of 17 degrees from the horizontal. In some examples, the third set of posts 454 on the bottom arm 465 mounted to or part of a surface that is set at an angle 484 of about 10 to about 25 degrees from the horizontal.

Figure 5:
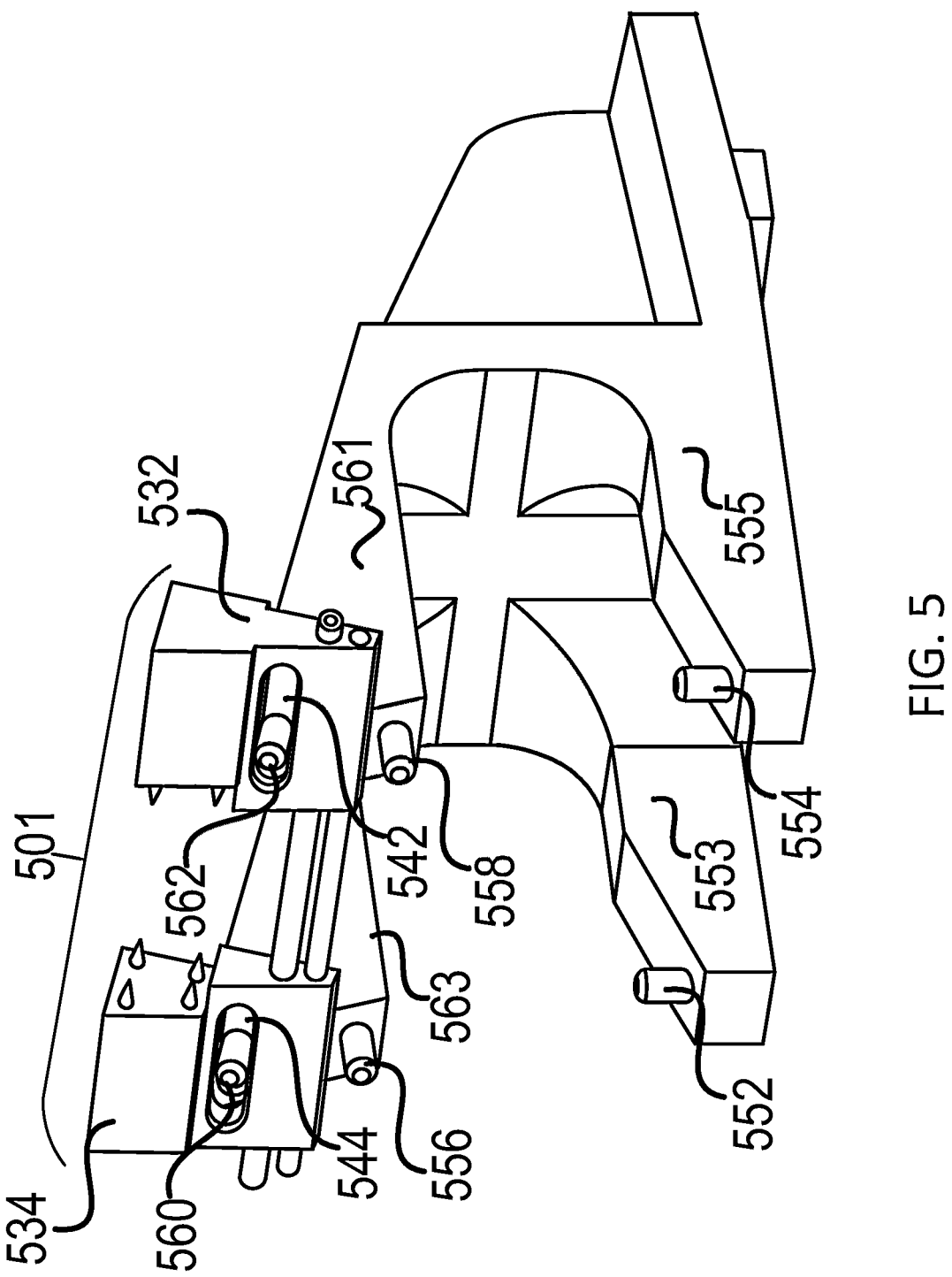
FIG. 5 is an example clamp and jig according to embodiments disclosed herein.

FIG. 5 is a diagram showing an example where the clamp 501 is mounted on the top posts 560, 562 of the top arms 561, 563. In the example, the other posts, the two other posts 556, 558 on the top arms 561, 563, and two posts 552, 554 on the bottom arms 553, 555, are not in use. As described herein, the clamp 501 can be mounted on the posts 560, 562 by the slots 542, 544 on the two blocks 532, 534 of the clamp 501. And due to the orientation of the clamp blocks 532, 534 and the arms 561, 563, the clamp 501 can only be arranged in one direction on each set of posts.

Not shown in FIG. 5 but the clamp can be mounted on any of the three sets of posts 560, 562, and 556, 558 and 552, 554 to achieve the preparation cuts. In side-on views in FIGS. 9-11, this is shown again.

Jig and Clamp Combination Examples

Figure 6:
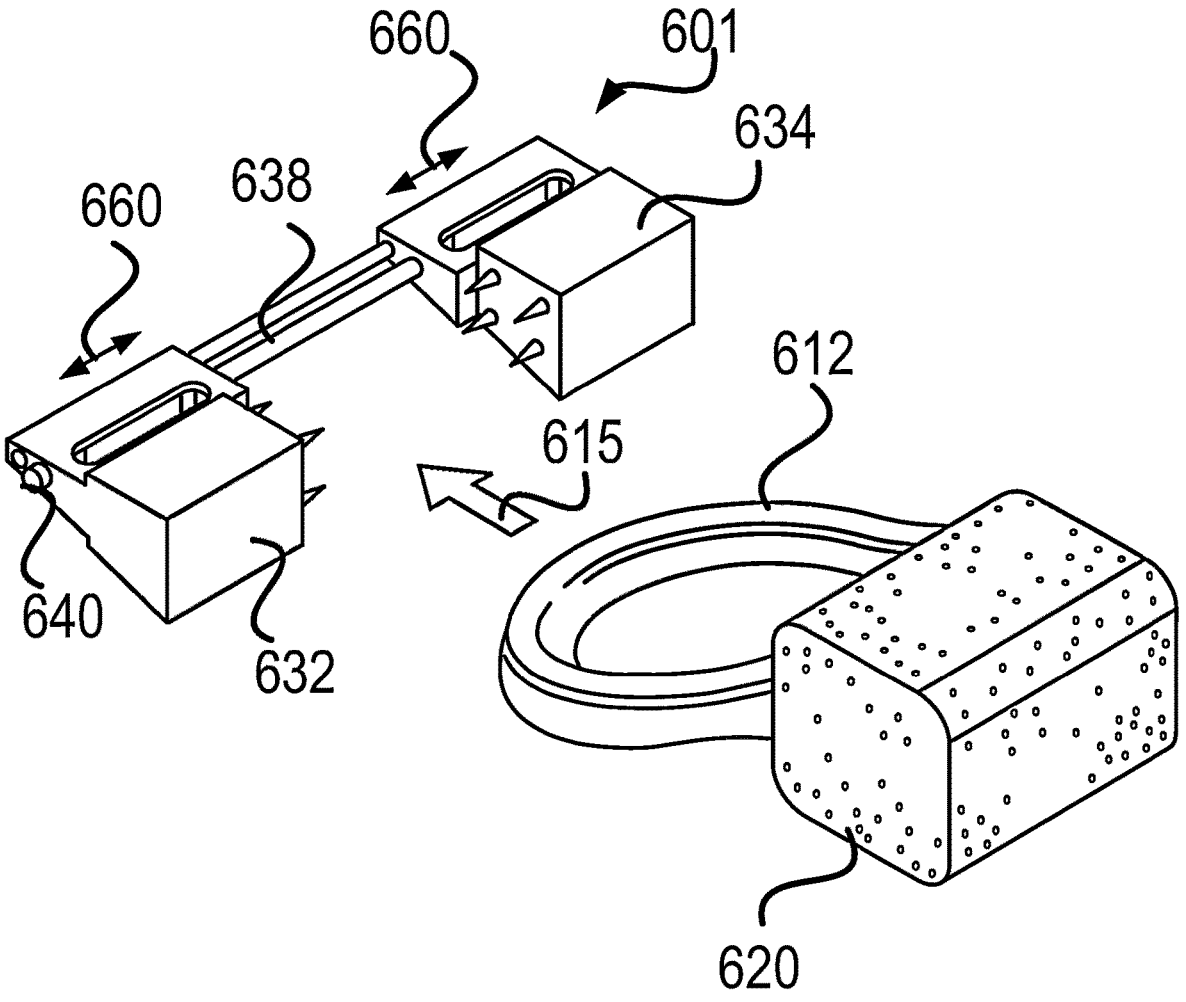
FIG. 6 is an example tissue specimen and clamp according to embodiments disclosed herein.

For examples where a jig and clamp combination are used, FIG. 6 shows an example where the bone block 620 and meniscus 612 is loaded into 615 the clamp 601. In the example, when the bone block 620 is moved between the two main blocks 632, 634 of the clamp, the screw bar 638 can be tightened 640 so that the internal threads in the corresponding holes in the blocks 632, 634, squeeze together 660 to tighten onto the bone block 620. If the screw bar 638 is turned the opposite direction, the main blocks 632, 634 can move away from one another, to loosen their grip on the bone block 620, depending on how the threads in the screw bar 638 and corresponding main block 632, 634 are arranged.

Figure 7:
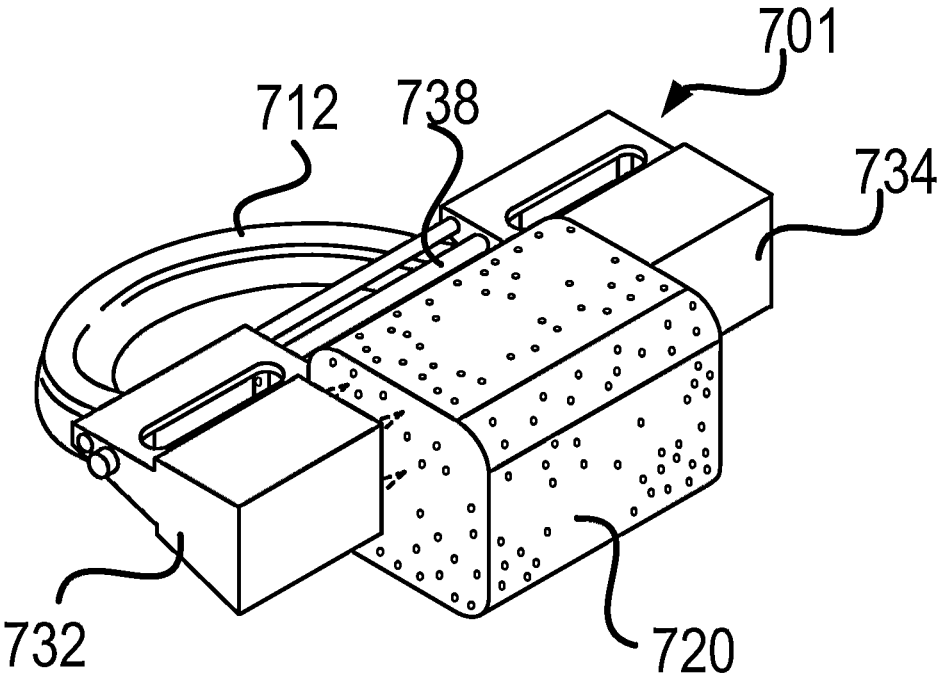
FIG. 7 is an example tissue specimen and clamp according to embodiments disclosed herein.

FIG. 7 shows the bone block 720 mounted in the clamp 701 between the main blocks 732, 734 with the meniscus 712. In such an orientation, the bone block 720 is firmly secured between the main blocks 732, 734 by tightening the screw bar 738 until the bone block is 720 held securely. In this manner, the portions of the bone block 720 which are to be cut away are exposed when viewed end-on, leaving the part of the bone block which is to be retained secured to the meniscus 712.

Figure 8:
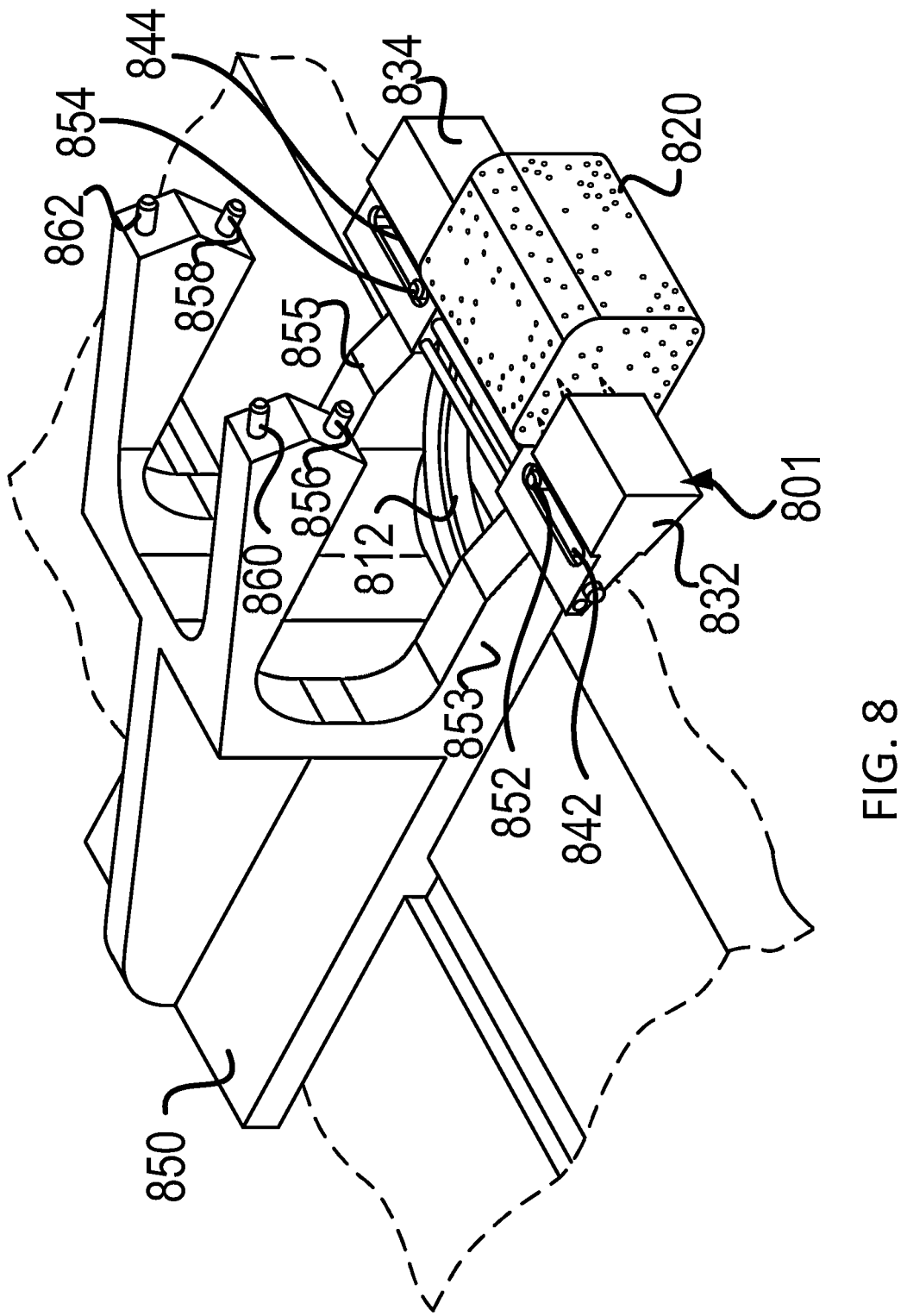
FIG. 8 is an example jig, tissue specimen, and clamp according to embodiments disclosed herein.

FIG. 8 shows an example of the bone block 820 secured in the clamp 801 between the two clamp blocks 832, 834 and the clamp 801 mounted on the two bottom arms 853, 855 and corresponding posts 852, 854. The posts 852, 854 on the jig bottom arms 853, 855 can mount onto or through the slots 842, 844 of the clamp 801. In this way, the bone block 820 is exposed along a line that is to be cut away as described herein (See FIGS. 9-11). Although not shown in FIG. 8, the other sets of posts 856, 858 and 860, 862 can also receive the clamp 801 and bone block 820 to expose the bone block 820 to the saw in the other orientations as described in FIGS. 9-11.

FIG. 9 is the first of three figures including FIGS. 10 and 11 which show a side-on view of the jig base 950 and mounted clamp 932 with one of the upper arms 961 and one of the lower arms 965. In the example, the clamp block 932 is mounted to the top post 962 on the top arm 961. In this orientation, the clamp block 932 exposes a portion 922 of the bone block 920 to a vertically oriented saw blade 990. In such an orientation, the meniscus 912 is safely out of the way of the saw blade 990 such that only the portion 922 exposed beyond the blade 990 can be cut off from the meniscus tissue 912, and the shape of the clamp block 932 shields the portion of the bone block 920 that is to be retained. The posts that are not used 954, 958 are also shown in FIG. 9 but utilized on the other two cuts shown in FIGS. 10 and 11. It should be noted that the cuts shown in FIGS. 9-11 can be made in any order, and the example order is not intended to be limiting.

FIG. 10 is the second of the three cuts shown in FIGS. 9-11 which show a side-on view of the jig base 1050 and mounted clamp 1032. In FIG. 10, the clamp block 1032 is mounted on the lower posts 1058 of the two sets of posts 1062, 1058 of the upper arm 1061. In such an orientation, only a portion 1022 of the bone block 1020 is exposed to the vertically oriented saw blade 1090 leaving the meniscus 1012 safely out of the way. The shape of the clamp block 1032 shields the portion of the bone block 1020 that is to be retained after the cut. The posts that are not used 1054 on the lower arm 1065, and 1062 on the top arm 1061 are also shown. It should be noted that the cuts shown in FIGS. 9-11 can be made in any order, and the example order is not intended to be limiting.

FIG. 11 is the third of the three cuts shown in FIGS. 9-11 which show a side-on view of the jig base 1150 and mounted clamp 1132. In FIG. 11, the clamp block 1132 is mounted on the posts 1154 of the lower arm 1165. In such an orientation, only a portion 1122 of the bone block 1120 is exposed to the vertically oriented saw blade 1190 leaving the meniscus 1112 safely out of the way. The shape of the clamp block 1132 shields the portion of the bone block 1120 that is to be retained after the cut. The posts that are not used 1162, 1168 on top arm 1161 are also shown. It should be noted that the cuts shown in FIGS. 9-11 can be made in any order, and the example order is not intended to be limiting.

In the examples described herein, the orientation of such a saw is vertical, or near vertical to the ground, or whatever surface the cutting is taking place. That is, the orientations described herein are in reference to a generally vertical saw blade interacting with the tissue to be cut. Such a disclosure is not limited to a vertical saw blade arrangement, and a jig and clamp system can be fashioned in a similar manner as described herein, but with a horizontal orientation, or other angled orientation. The system can be arranged such that the relative angles between the saw, clamp, and jig however, would result in similar cuts to the meniscal bone block to obtain the desired shape. Therefore, the terms regarding orientation of the saw, jig, and/or clamp are not intended to be limiting.

Example Steps

In general, the systems described herein can be utilized in methods to shape a meniscal bone block.

In a method, a clamp can be attached to a bone block of meniscal tissue, wherein a generally trapezoidal shape of the clamp can guide a saw to shape the bone block.

In some example methods without using a jig, cuts can be made to the meniscal tissue around the three sides of the clamp trapezoidal shape. In some example methods using a jig, the clamped tissue can be positioned on a jig and a generally vertical cut can be made on the bone block along one side of the clamp trapezoidal shape.

In the jig method, the clamped tissue can be placed on the jig in position two and another generally vertical cut on the bone block can be made along one side of the clamp trapezoidal shape.

In the jig method, the clamped tissue can be placed on the jig in position three and another generally vertical cut on the bone block can be made along one side of the clamp trapezoidal shape.

In the methods, the clamped tissue, having been prepared with or without a jig now possesses the shape required to insert into the knee of the patient for transplant as described herein. It need only be clamped to the tissue once, and the three cuts made, thereby minimizing the damage to the tissue, and easing the workload for the person preparing the tissue. The clamp can be removed and the tissue inserted as described.

It should be noted that these steps can be performed in any order. That is, once the clamp is attached to the meniscal bone block, the order of the cuts can be different than that described above or FIGS. 9-11. No one order is necessarily better than any order, as long as all three cuts are made to the tissue, therefore the listing of the steps above are not intended to be limiting in terms of order.

Implant Fitting

Figure 12:
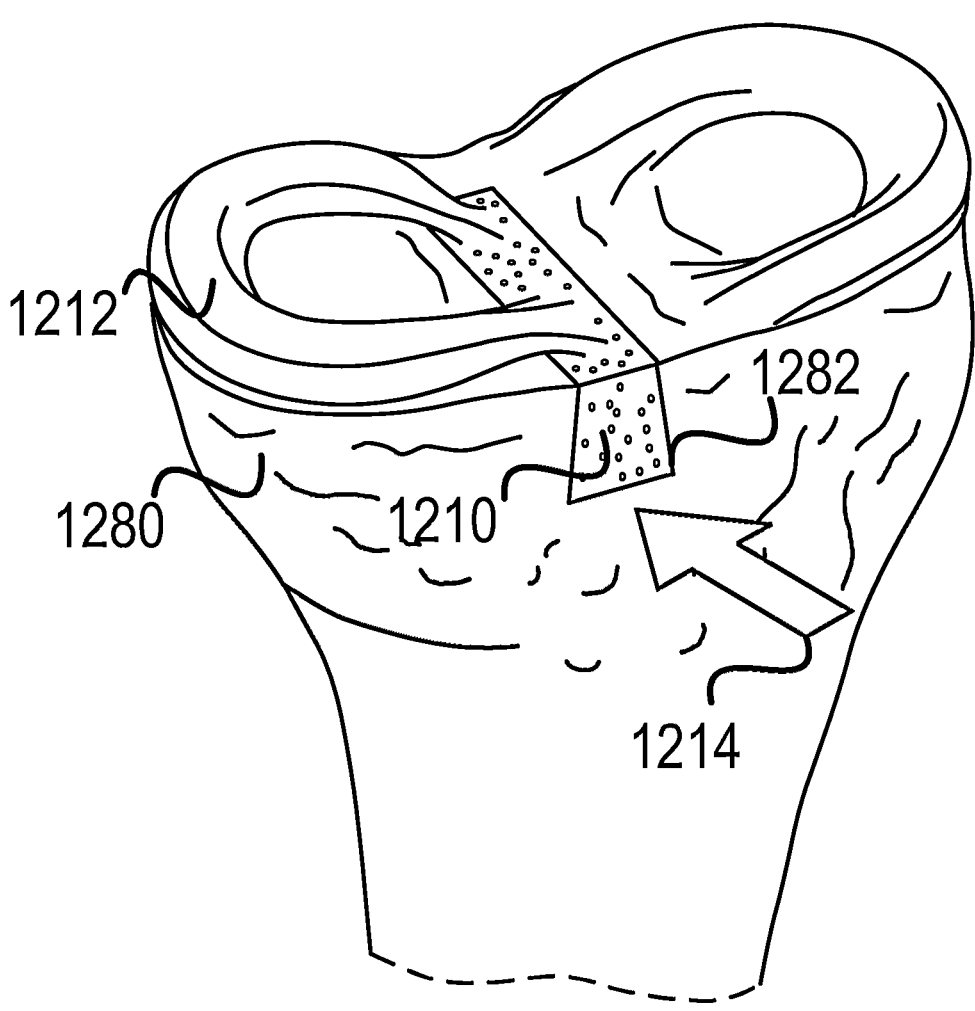
FIG. 12 is an example applied prepared tissue specimen according to embodiments disclosed herein.

FIG. 12 shows an example of a resulting dove tail or trapezoidal shaped bone block 1210 and attached meniscus 1221 being mounted into the knee 1280 of the patient by sliding 1214 the dove tail shape of the bone block 1310 into the corresponding groove 1282. This anatomical reconstruction of the meniscus uses the shaped bone block 1210 of a meniscal allograft into a keyhole plug to match a corresponding keyhole groove 1282 prepared through the cortical and cartilaginous surface of the tibial plateau 1280. The bone plug or block 1210 for the meniscal allograft is then fed into the keyhole groove 1282, such that the meniscal allograft is mounted on the tibial plateau and secured without transosseous sutures. In such a way, the meniscus 1212 can rest where it is needed on the knee joint, and the bone block 1210 can hold the tissue in place due to its shape and corresponding slot in the knee bone of the patient.

In some examples, a trapezoidal shape is not used, and a generally rectangular shape is used instead. In such examples, the tissue can be prepared with a generally rectangular shape by utilizing a clamp with a corresponding shape, or by further preparing the tissue by administering an additional cut as described herein. In such examples, the corresponding keyhole groove 1282 would be shaped so as to match the shape of the tissue, whether that be a generally trapezoidal shape, generally rectangular shape, or any other corresponding shape.

Examples of Clamps

Figure 13A:
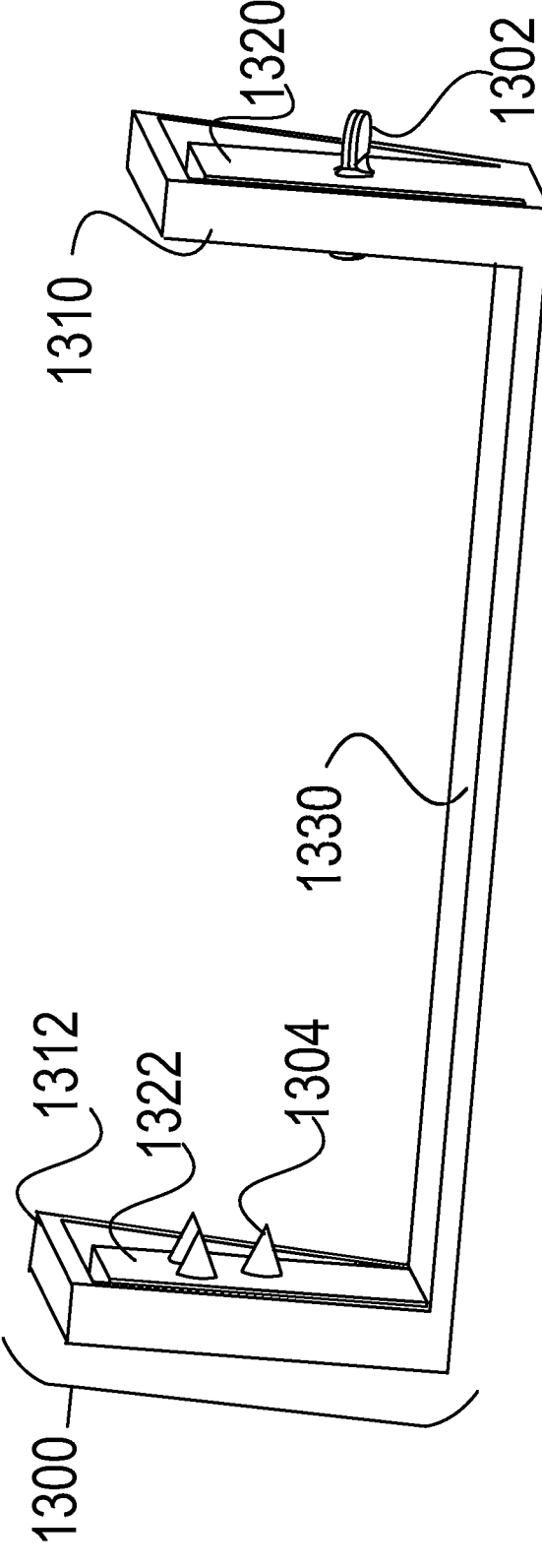
FIGS. 13A and 13B show another example clamp according to embodiments disclosed herein.
Figure 13B:
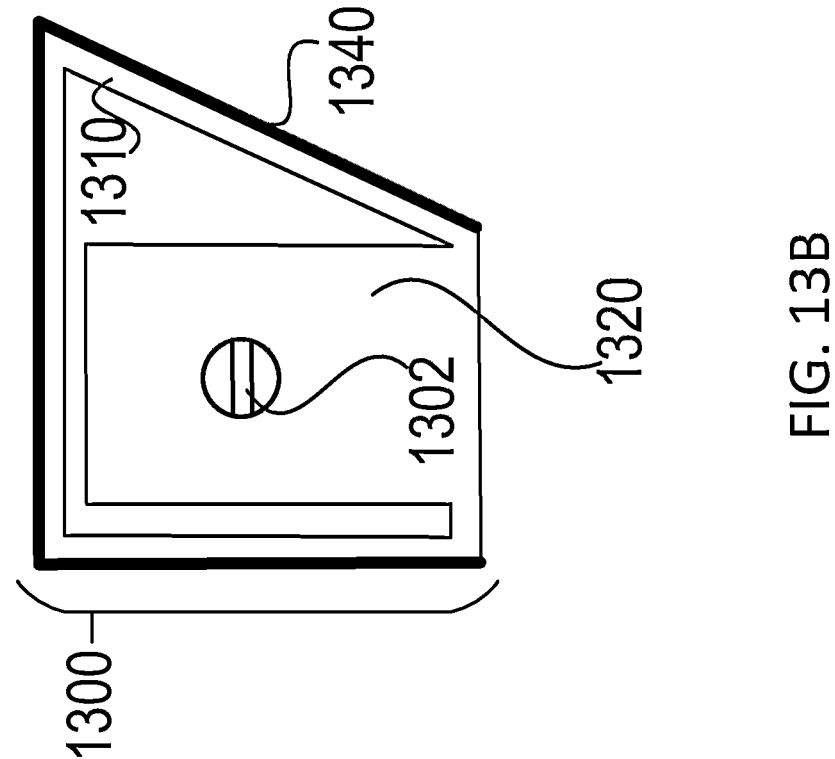

FIG. 3A shows one example clamp arrangement with a bar and screw threads. Other example clamps with different features can be arranged to clamp the tissue for preparation as described herein. FIGS. 13A and 13B show another example clamp 1300 embodiment with a set screw 1302 on one end to secure a tissue sample instead of a threaded bar as shown in FIG. 3A. FIG. 13A shows a friction sided clamp with spikes 1304, knurl bars, and/or other friction features on the other end. In such an example, the set screw 1302 can be secured on one side 1310 of the clamp and be a threaded screw capable of being screwed toward or away from the opposing side 1310 of the clamp, thereby pinching, holding, securing, and/or otherwise retaining a bone block tissue specimen (not shown) placed in the clamp as described herein. Such an embodiments would not require the threaded screw bar to run the length of the clamp as it does in the embodiment of FIG. 3A.

In the example of FIG. 13A, the end of the clamp with the set screw 1310 and friction components 1312 are each mounted on a tongue 1320, 1322 which is surrounded by a respective frame 1310, 1312. In such a configuration, each tongue 1320, 1322 is connected to the base of the clamp 1330 but free from the clamp and free from each respective frame 1310, 1312, on the other sides, leaving it able to flex, bend, or deflect slightly within the framed portions 1310, 1312, respectively due to the material of the clamp. Such a flexing of the tongue may depend on the thickness of the material of the clamp, and/or the material of the clamp, but such a flexing may be slight and allow for a tightening of the set screw 1302 or other fastener to hold the tissue but cause the least amount of damage to it. In some examples, instead of or in addition to the set screw 1310, a k-wire, ratchet, or other system can secure the tissue in place, the example of a set screw is not intended to be limiting.

FIG. 13B shows an end-on view of the clamp 1300 with the tongue 1320 and frame 1310 configuration. Such an arrangement can allow for the set screw 1302 and friction fit components (1304 in FIG. 13A) to flex slightly when a tissue bone block is mounted in the clamp 1300 and the set screw 1302 tightened as described, yet still keep the frame 1310, (1312 in FIG. 13A) and its end-on shape 1340 in place for the user to use as a guide when cutting the bone block tissue specimen as described herein. (See FIG. 3B for discussion of angles of the end-on side of the clamp.)

Once secure, the edges or sides of the clamp 1340 can be used as a guide for a saw blade to cut away the bone block portions as described in FIGS. 9-11 leaving the desired shape of bone block for insertion into a patient knee as described in FIG. 12.

As described, by securing the clamp 1300 only once, and being able to guide all the necessary cuts to form the desired shape, the systems and methods here allow for a more accurate tissue preparation, which is easier for the human user, and with less damage to the tissue sample used for the transplant. This is due, at least in part, to the ability for the preparation to be made with only one clamp applied one time to the tissue.

The clamp 1300 described herein can be made of any material suitable for preparing the tissue as described. The material can be sturdy, solid, easy to clean and sterilize, and resilient to corrosion. In some examples, the clamp can be made of metal such as aluminum, steel, iron, brass, copper, and/or an alloy of any of these or other metals, fiberglass, carbon fiber, ceramics, or other non-metal material alone or in combination.

In some examples, once the clamp 1300 is positioned on the tissue, cuts to the tissue, which follow the sides of the clamp 1340 can be made without a jig. In some examples, the clamp 1300 may include slots in order for it to be used in conjunction with a jig as described in embodiments above. In such examples, the slots (not pictured) are or are not present to be utilized in performing the preparation of the tissue specimen. In examples without a jig, a user can hold the clamped tissue and administer the cuts needed without utilizing a jig arrangement. Saws such as a sagittal saw can be useful in such examples, and by using such a saw, the jig arrangement can be unnecessary for tissue preparation. In examples, with a jig, the clamp 1300 may be mounted on the jig as described above, to make cuts using a band saw or other saw. The embodiments showing jig slots on the clamp or not in FIGS. 3A and 13A are not intended to be limiting and the jig slot features may be utilized on either arrangement.

Examples of Slot Cut Jig

In use, a surgeon may desire a bone plug or block shape that includes a dovetailed triangular portion as shown in FIG. 2. In some examples, a different shape, such as a more rectangular shape may be desired. It would be therefore beneficial to allow the surgeons the option to retain the full dovetailed trapezoidal shape including the triangular portion for surgery, or, be able to easily remove the triangular portion to retain a more rectangular shape of the bone block.

Figure 14:
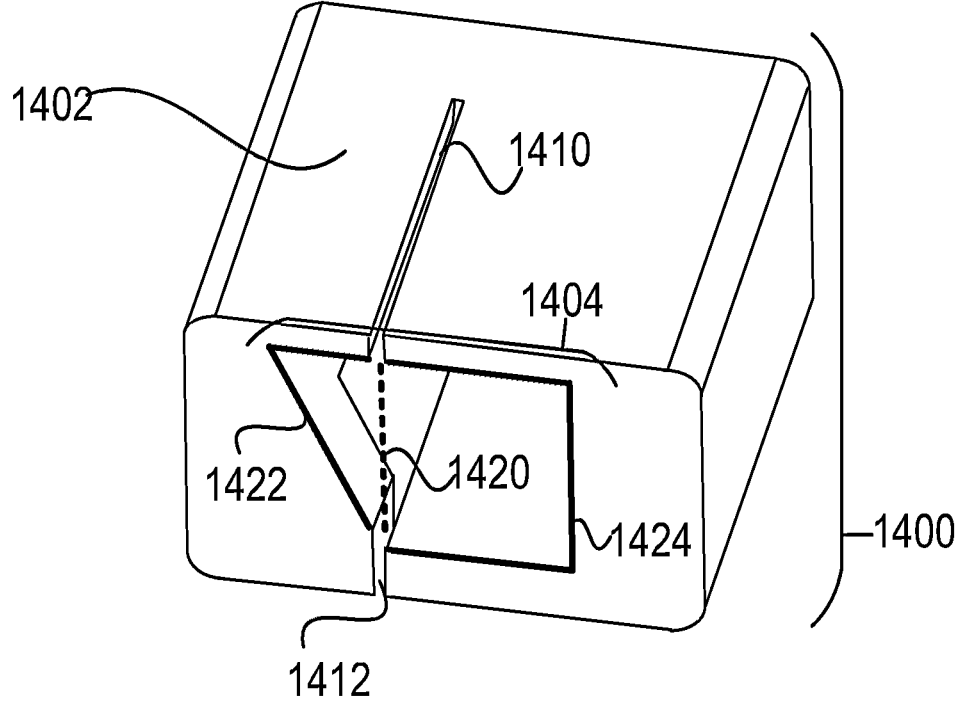
FIG. 14 is an example slot cut jig according to embodiments disclosed herein.

FIG. 14 shows an example slot cut jig 1400 arrangement which can be used to further prepare tissue, even after it has first been shaped into a triangular bone block as described herein. In the example, the slot cut jig 1400 includes a top 1402, and a main slot 1404 through the slot cut jig 1400 for the tissue plug (not pictured) to fit into, with the meniscus hanging out below. The slot cut jig 1400 can include an upper saw slot 1410 in the top 1402 and lower saw slot 1412 for a saw blade to pass 1420 which would allow for the optional further preparation of the tissue by a surgeon. Using such a saw slot 1410, 1412, can guide a saw blade in a direction 1420 that removes a triangular portion 1422 of the dove tail but leaves the generally rectangular shape 1424 in place, still attached to the meniscus (not shown). The slot cut jig 1400 can hold the bone block tissue in place allowing for easier handling of the tissue during preparation and cutting.

The slot cut jig 1400 can also be used for transportation of the tissue in order to help protect the tissue from jarring, scraping, bumping, or other damaging incidents. In such an example, a preparation team may prepare the tissue and place it into the slot cut jig 1400 to protect it during transportation. Once the tissue is placed in the slot cut jig 1400, with the main slot 1404 surrounding most of the bone block and the meniscus hanging out, the slot cut jig 1400 and tissue sample (not pictured) can be packed in ice, a thermal insulating container, and/or otherwise prepared and shipped or otherwise transported to a surgical facility for further preparation and/or insertion into a patient. In such a way, the slot cut jig 1400 may act as both a protective device and one allowing for easy preparation of bone shape adjustments.

Such a slot cut jig 1400 can be made of similar or the same material as the clamp and/or jig, including but not limited to metal such as aluminum, steel, iron, brass, copper, and/or an alloy of any of these or other metals, fiberglass, carbon fiber, ceramics, or other non-metal material alone or in combination.

From the foregoing, it will be appreciated that specific embodiments of the description have been described herein for purposes of illustration, but that various modifications can be made without deviating from the spirit and scope of the various embodiments of the description. Further, while various advantages associated with certain embodiments of the description have been described above in the context of those embodiments, other embodiments can also exhibit such advantages, and not all embodiments need necessarily exhibit such advantages to fall within the scope of the description. Accordingly, the description is not limited, except as by the appended claims.

While the above description describes various embodiments of the description and the best mode contemplated, regardless how detailed the above text, the description can be practiced in many ways. Details of the system can vary considerably in its specific implementation, while still being encompassed by the present disclosure. As noted above, particular terminology used when describing certain features or aspects of the description should not be taken to imply that the terminology is being redefined herein to be restricted to any specific characteristics, features, or aspects of the description with which that terminology is associated. In general, the terms used in the following claims should not be construed to limit the description to the specific examples disclosed in the specification, unless the above Detailed Description section explicitly defines such terms. Accordingly, the actual scope of the description encompasses not only the disclosed examples, but also all equivalent ways of practicing or implementing the description under the claims.

The teachings of the description provided herein can be applied to other systems, not necessarily the system described above. The elements and acts of the various examples described above can be combined to provide further implementations of the description. Some alternative implementations of the description can include not only additional elements to those implementations noted above, but also can include fewer elements. Further any specific numbers noted herein are only examples: alternative implementations can employ differing values or ranges.

References throughout the foregoing description to features, advantages, or similar language do not imply that all of the features and advantages that can be realized with the present description should be or are in any single embodiment of the description. Rather, language referring to the features and advantages is understood to mean that a specific feature, advantage, or characteristic described in connection with an embodiment is included in at least one embodiment of the present description. Thus, discussion of the features and advantages, and similar language, throughout this specification can, but do not necessarily, refer to the same embodiment.

Furthermore, the described features, advantages, and characteristics of the present description can be combined in any suitable manner in one or more embodiments. One skilled in the relevant art will recognize that the present description can be practiced without one or more of the specific features or advantages of a particular embodiment. In other instances, additional features and advantages can be recognized in certain embodiments that cannot be present in all embodiments of the present description.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." Any of the terms "comprising", "consisting essentially of", and "consisting of" can be replaced with either of the other two terms, while retaining their ordinary meanings. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105). Any single term, single element, single phrase, group of terms, group of phrases, or group of elements described herein can each be specifically excluded from the claims. As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number can also include the plural or singular number respectively. The word "or," in reference to a list of two or more items, covers all of the following interpretations of the word: any of the items in the list, all of the items in the list, and any combination of the items in the list.

Although certain aspects of the description are presented below in certain claim forms, the applicant contemplates the various aspects of the description in any number of claim forms. Accordingly, the applicant reserves the right to pursue additional claims after filing this application to pursue such additional claim forms, in either this application or in a continuing application.

What is claimed is:

1. A system for preparing a meniscal tissue for implant, comprising:

a jig with a base, two lower jig arms, and two upper jig arms;

a clamp with a first block having a first slot and a second block having a second slot, the first block and the second block connected by a threaded screw rod that allows the first block and the second block to be moved closer or farther from one another through corresponding screw threads;

the jig having three pairs of posts, a first pair of posts located on a top of the two upper jig arms, a second pair of posts located on a middle of the two upper jig arms, and a third pair of posts located on a top of the two lower jig arms, wherein the first block and the second block are configured to mount on each of the three pairs of posts by the first slot and the second slot in each of the respective first and second blocks, wherein when the clamp is mounted to one of the three pairs of posts the jig and clamp are configured to guide sawing a meniscal tissue bone block secured in the clamp to obtain a shape that is generally of the same shape as the clamp first block and the second block; and wherein each of the first block and the second block are configured to secure a bone block and meniscal tissue.

2. The system of claim 1 wherein the clamp includes a slide rod mounted in parallel to the threaded screw rod in the first block and the second block.

3. The system of claim 1 wherein the first block and second block have a generally trapezoidal end-on shape, the trapezoidal shape including a first side, a second bottom side, a third side, and a top side.

4. The system of claim 3 wherein the top of the two upper jig arms and the first side allow for the clamp to mount to the first pair of posts on the top of the two upper jig arms.

5. The system of claim 3 wherein the top of the two upper jig arms and the third side allow for the clamp to mount to the second pair of posts on the middle of the two upper jig arms.

6. The system of claim 3 wherein the top of the two bottom jig arms and the first clamp side allow for the clamp to mount to the third pair of posts on the top of the two lower jig arms.

7. The system of claim 1 wherein each of the first block and second block comprise spikes, knurls, set screws, or bumps configured to secure the bone block and meniscal tissue.

8. The system of claim 3 wherein the top of the two upper jig arms and the first side allow for the clamp to mount to the first pair of posts on the top of the two upper jig arms, and wherein the top of the two upper jig arms and the third side allow for the clamp to mount to the second pair of posts on the middle of the two upper jig arms, and wherein the top of the two bottom jig arms and the first side allow for the clamp to mount to the third pair of posts on the top of the two lower jig arms, such that a vertically arranged saw blade can make three cuts to the bone block secured between the first block and the second clamp block, when the clamp is mounted on the three pairs of posts, and result in a bone block that is generally of the same trapezoidal shape as the end-on clamp shape.

9. The system of claim 1 wherein the two lower jig arms include a surface that is sloped about 15 to about 20 degrees from horizontal.

10. The system of claim 1 wherein the two upper jig arms comprise a top portion that includes a surface that is sloped about 60 to about 80 degrees from horizontal.

11. The system of claim 1 wherein the two upper jig arms comprise a middle portion that includes a surface that is sloped about 60 to about 80 degrees from horizontal.

12. A system for preparing a meniscal tissue for implant, comprising a jig and a clamp combination, configured such that the clamp includes two clamp mounting surfaces on each of a first block and a second block, and the jig includes three jig mounting surface post pairs on an upper pair of arms and a lower pair of arms, the two clamp mounting surfaces and the three jig mounting surface post pairs are configured to mate to secure the clamp in each of three positions on the three jig mounting surface post pairs;

wherein the first block and the second block are connected by a threaded screw, wherein the first block is configured to mount to one of the three jig mounting surface post pairs and the second block is configured to mount to one of the three jig mounting surface post pairs, and wherein the first block and the second block are configured to secure a tissue sample between the first block and the second block.

13. The system of claim 12 wherein two of the jig mounting surface post pairs are on the upper pair of arms and one of the pairs of jig mounting surface post pairs are on the lower pair of arms.

14. The system of claim 12 wherein the first block and the second block have a generally trapezoidal shape when viewed end-on.

* * * * *